(12) United States Patent
Minoda et al.

(10) Patent No.: US 9,726,649 B2
(45) Date of Patent: *Aug. 8, 2017

(54) CHROMATOGRAPHIC MEDIUM

(71) Applicant: DAICEL CORPORATION, Osaka-shi, Osaka (JP)

(72) Inventors: Toshiharu Minoda, Myoko (JP); Isamu Ikeda, Myoko (JP)

(73) Assignee: DAICEL CORPORATION, Osaka-shi, Osaka (JP)

(*) Notice: Subject to any disclaimer, the term of this patent is extended or adjusted under 35 U.S.C. 154(b) by 382 days.

This patent is subject to a terminal disclaimer.

(21) Appl. No.: 14/363,515

(22) PCT Filed: Jan. 9, 2013

(86) PCT No.: PCT/JP2013/050176
§ 371 (c)(1),
(2) Date: Jun. 6, 2014

(87) PCT Pub. No.: WO2013/105572
PCT Pub. Date: Jul. 18, 2013

(65) Prior Publication Data
US 2014/0360927 A1    Dec. 11, 2014

(30) Foreign Application Priority Data

Jan. 11, 2012  (JP) ................................ 2012-003378

(51) Int. Cl.
B01D 15/08    (2006.01)
B01J 20/285    (2006.01)
(Continued)

(52) U.S. Cl.
CPC ............. G01N 30/92 (2013.01); B01D 15/08 (2013.01); B01J 20/291 (2013.01); G01N 30/93 (2013.01);
(Continued)

(58) Field of Classification Search
CPC ........ B01D 15/08; G01N 30/90; G01N 30/92; G01N 30/93; G01N 30/94;
(Continued)

(56) References Cited

U.S. PATENT DOCUMENTS 3,591,805 A    7/1971 Schoeffel
3,914,174 A    10/1975 Fuchs
(Continued)

FOREIGN PATENT DOCUMENTS

CH    574 603 A5    4/1976
CN    103842812 A   6/2014
(Continued)

OTHER PUBLICATIONS

Daicel Corp., "2D-ChiralTLC IA/IC," Sep. 2011, 6 pages.*
(Continued)

*Primary Examiner* — Katherine Zalasky
(74) *Attorney, Agent, or Firm* — Flynn, Thiel, Boutell & Tanis, P.C.

(57) ABSTRACT

A chromatographic medium having a separating agent layer, which is used to separate target substances, and a permeation layer, which is laminated so as to face the separating agent layer and which is used to enable permeation of the target substances separated by the separating agent layer, wherein a region in which the permeation layer is not laminated is present on a part of the separating agent layer, the separating agent layer exhibits a separating property for the target substances and exhibits an optical responsiveness to ultraviolet rays, and the permeation layer exhibits an optical responsiveness that is different from those of the target substances and the separating agent layer.

10 Claims, 5 Drawing Sheets

(a)        (b)

(51) Int. Cl.
*G01N 30/93* (2006.01)
*G01N 30/92* (2006.01)
*B01J 20/291* (2006.01)
B01J 20/32 (2006.01)
G01N 30/94 (2006.01)
G01N 30/88 (2006.01)

(52) U.S. Cl.
CPC ... *B01J 2220/80* (2013.01); *G01N 2030/8877* (2013.01)

(58) Field of Classification Search
CPC ....... G01N 2030/945; G01N 2030/8877; B01J 20/291; B01J 2220/80
See application file for complete search history.

(56) References Cited

U.S. PATENT DOCUMENTS

| | | | |
|---|---|---|---|
| 4,313,906 A * | 2/1982 | Filipi | G01N 30/92 210/198.3 |
| 4,348,286 A | 9/1982 | Felton | |
| 4,786,415 A * | 11/1988 | Shibata | B01D 15/08 210/198.2 |
| 5,306,645 A * | 4/1994 | Yamamoto | G01N 30/94 210/198.3 |
| 5,773,576 A | 6/1998 | Junker-Buchheit et al. | |
| 6,787,366 B1 * | 9/2004 | Novak | G01N 31/22 210/634 |
| 2001/0051350 A1 * | 12/2001 | Nazareth | G01N 33/558 435/7.5 |
| 2013/0067996 A1 | 3/2013 | Minoda et al. | |
| 2014/0248196 A1 | 9/2014 | Minoda et al. | |

FOREIGN PATENT DOCUMENTS

| | | |
|---|---|---|
| JP | 03-063567 A | 3/1991 |
| JP | 3140138 B2 | 9/1993 |
| WO | WO 2008/156080 A1 | 12/2008 |
| WO | WO 2011/106694 A1 | 9/2011 |
| WO | WO 2011/149041 A1 | 12/2011 |

OTHER PUBLICATIONS

Extended European Search Report issued in corresponding European Application No. 13735868.5, dated Sep. 16, 2015 (6 pages).
Office Action of Chinese Patent Office issued in Application No. 201380005303.6 with English translation dated Feb. 16, 2015 (17 pages).
Form PCT/ISA/210 International Search Report issued in International Application No. PCT/JP2013/050176 with English translation, date of mailing Apr. 16, 2013 (3 pages).

* cited by examiner

[Fig.1]
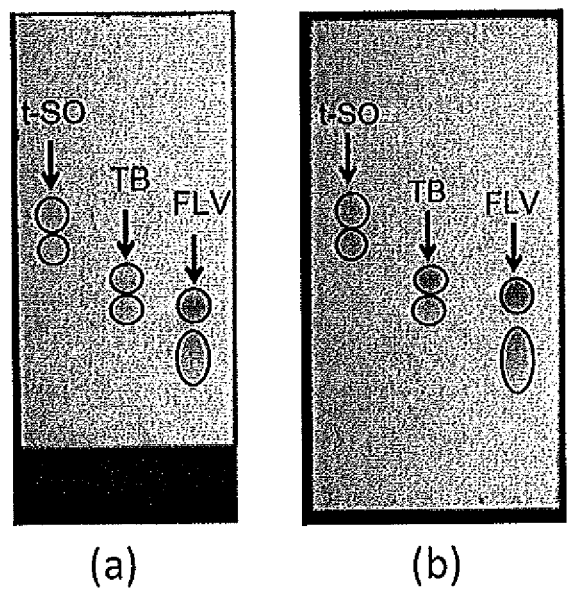
(a)   (b)
[Fig.2]
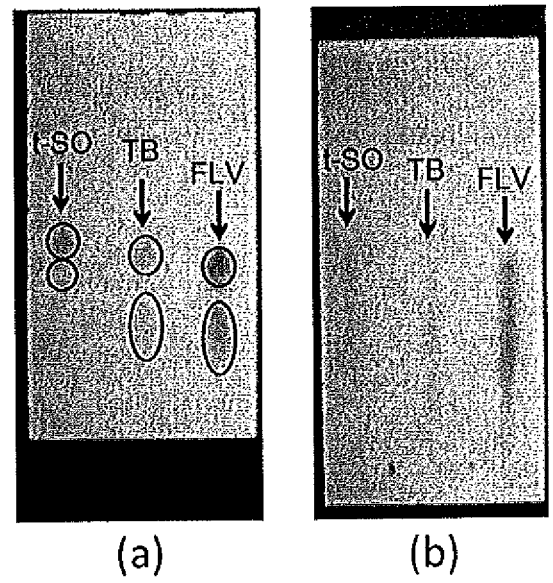
(a)   (b)

[Fig.3]
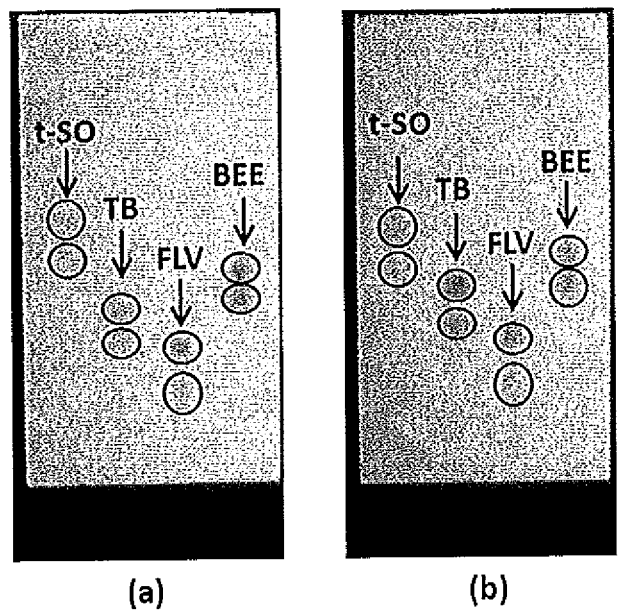
(a)  (b)
[Fig.4]
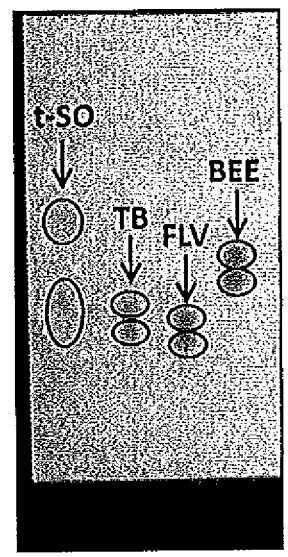 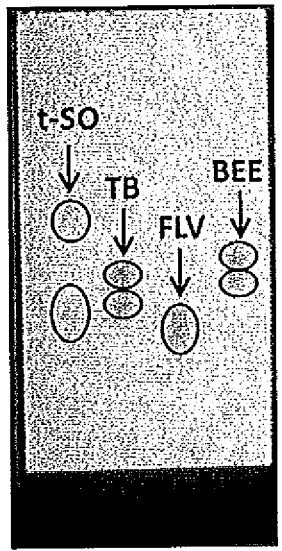
(a)  (b)

[Fig.5]
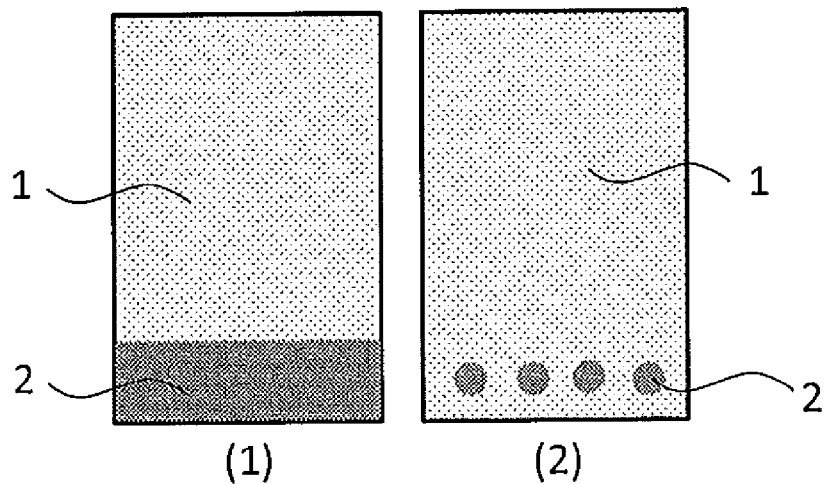
(1)    (2)
[Fig.6]
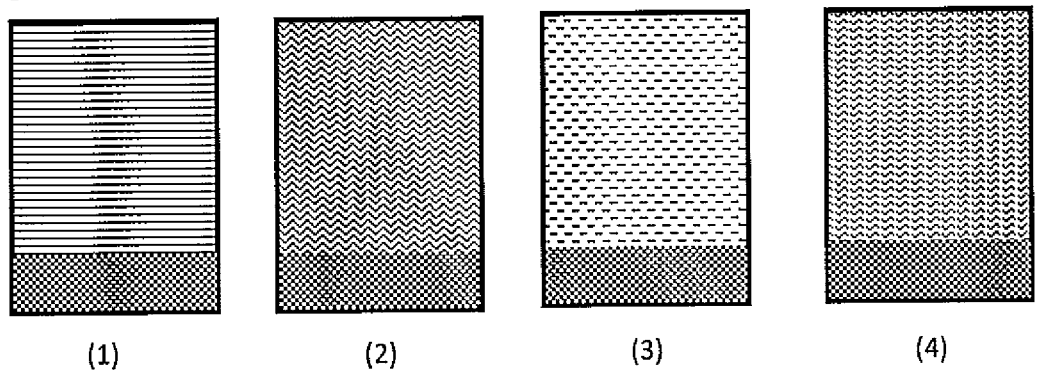
(1)    (2)    (3)    (4)
[Fig.7]
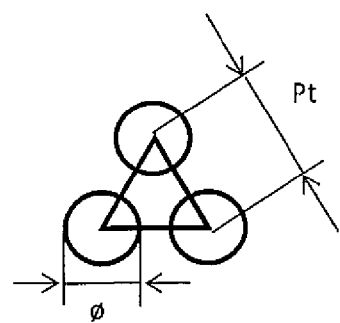

[Fig.8]
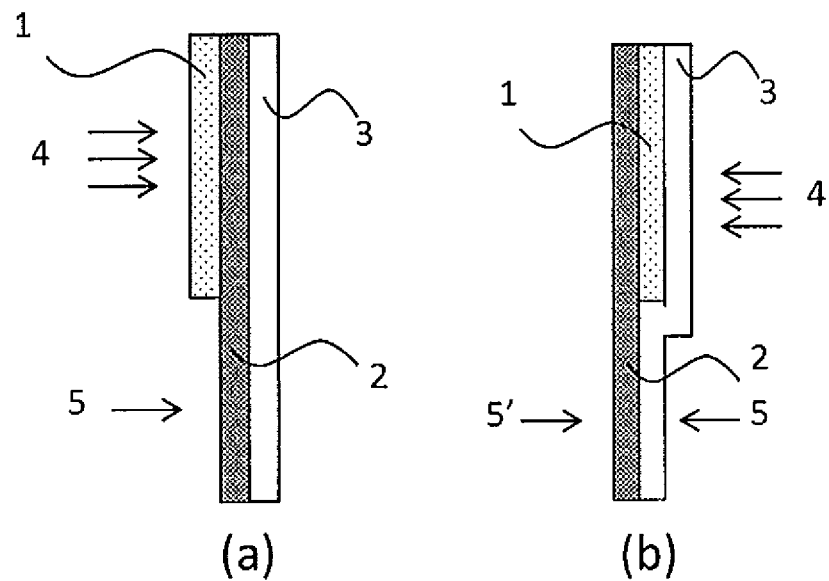
[Fig.9]
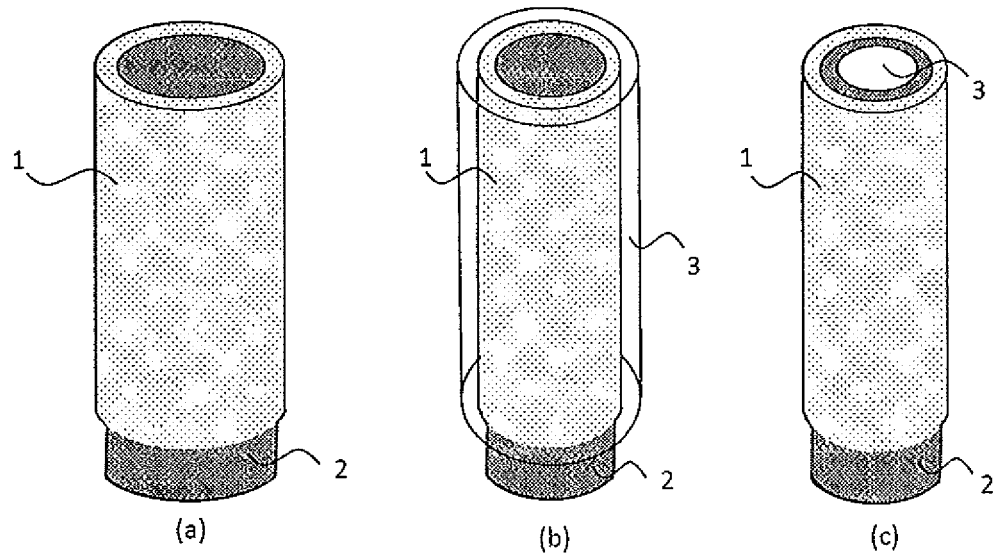

[Fig.10]
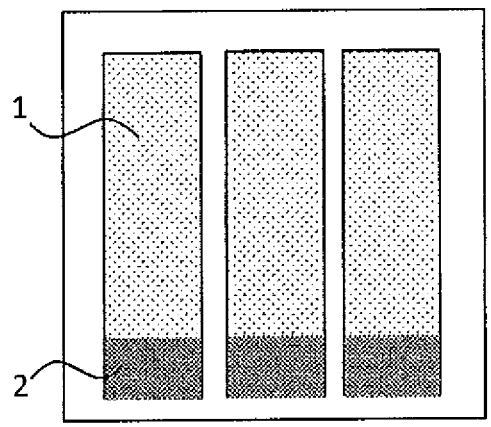
[Fig.11]
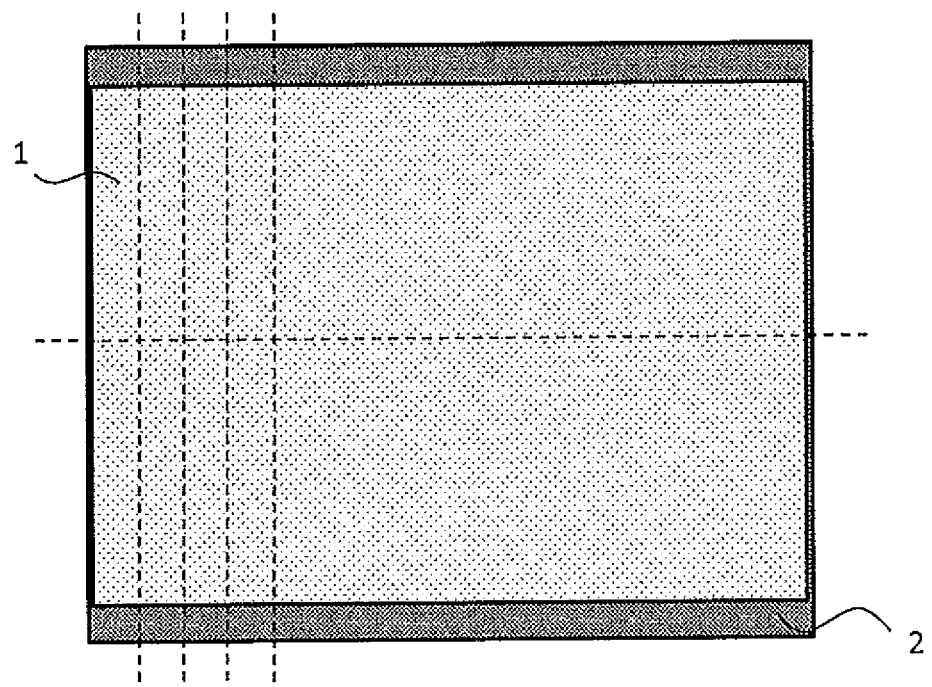

CHROMATOGRAPHIC MEDIUM

TECHNICAL FIELD

The present invention relates to a chromatographic medium having two layers having a different optical responsiveness to ultraviolet rays.

BACKGROUND ART

Thin layer chromatography (hereinafter also referred to as "TLC") is known as a method for separating and detecting specific components in a mixture. When separating components by means of TLC, detection is achieved by subjecting spots, which are obtained by developing a sample, to irradiation with ultraviolet rays or to a coloration treatment using a coloring reagent on the basis of differences in the optical responsiveness of, for example, a separating agent layer and the components being detected.

Meanwhile, separating agents that contain polysaccharide derivatives such as phenyl esters of polysaccharides are known as separating agents for optical isomers. When used in separating agent layers for TLC plates, such separating agents that contain aromatic rings are, in some cases, unable to detect components to be detected when irradiating with ultraviolet rays or carrying out a coloration treatment using a coloring reagent.

As means for solving this type of problem, a TLC plate is known in which a first separating agent layer, which can achieve the separation of target substances but does not exhibit an optical responsiveness, and a second separating agent layer, which does not achieve a separation function but exhibits an optical responsiveness, are formed side-by-side on the same substrate (for example, see patent document 1). In this TLC plate, target substances are developed from the first separating agent layer to the second separating agent layer, spots separated by the first separating agent layer migrate to the adjacent second separating agent layer and are detected there according to their optical responsiveness.

In this TLC plate, the extract component that is readily adsorbed by the first separating agent layer does not, in some cases, satisfactorily reach the second separating agent layer. In addition, because the speed of migration of a spot of a target substance in a sample generally varies in each separating agent layer, the positional relationship of spots in a first separating agent layer is not necessarily precisely maintained in a second separating agent layer. Therefore, it is not necessarily possible to precisely detect the state of separation in the first separating agent layer in the aforementioned TLC plate, and further research is needed in this respect at least.

Patent Document 1: Japanese Patent No. 3140138

The present invention provides a chromatographic medium which can separate and detect target substances in a sample using a single kit.

The inventors of the present invention found that the aforementioned problems could be solved by using a chromatographic medium having a separating agent layer, which is used to separate target substances, and a permeation layer, which is laminated so as to face the separating agent layer and which is used to enable permeation of the target substances separated by the separating agent layer, wherein a region in which the permeation layer is not laminated, that is, a region where only the separating agent layer is present, is present on a part of the separating agent layer, a layer that exhibits a separating property for the target substances and exhibits an optical responsiveness to ultraviolet rays is used as the separating agent layer, and a layer that exhibits optical response properties that are different from those of the separating agent layer is used as the permeation layer, and thereby completed the present invention.

That is, the present invention provides a chromatographic medium having a separating agent layer, which is used to separate target substances, and a permeation layer, which is laminated so as to face the separating agent layer and which is used to enable the permeation of the target substances separated by the separating agent layer, wherein regions in which the permeation layer is not laminated are present on a part of the separating agent layer, the separating agent layer exhibits the separability of the target substances and an optical responsiveness to ultraviolet rays, and the permeation layer exhibits an optical responsiveness that is different from those of the target substances and the separating agent layer.

<1> A chromatographic medium having a separating agent layer, which is used to separate target substances, and a permeation layer, which is laminated so as to face the separating agent layer and which is used to enable permeation of the target substances separated by the separating agent layer, wherein a region in which the permeation layer is not laminated is present on a part of the separating agent layer, the separating agent layer exhibits a separating property for the target substances and an optical responsiveness to ultraviolet rays, and the permeation layer exhibits an optical responsiveness that is different from those of the target substances and the separating agent layer.

<2> The chromatographic medium according to <1>, wherein the region in which the permeation layer is not laminated on a part of the separating agent layer is present in a region of the chromatographic medium between a dip end part, which is dipped in a developing solution used to develop the target substances, and half the length of the chromatographic medium in a direction of development.

<3> The chromatographic medium according to <1> or <2>, wherein the permeation layer is laminated in a discontinuous manner in the direction of development of the chromatographic medium.

<4> The chromatographic medium according to any one of <1> to <3>, wherein the permeation layer is laminated in the dotted manner on the separating agent layer.

<5> The chromatographic medium according to <4>, wherein in the permeation layer laminated in the dotted manner, the average diameter of the dots is 0.01 to 5 mm and the pitch between dots is 0.015 to 5 mm.

<6> The chromatographic medium according to any one of <1> to <3>, wherein the permeation layer is laminated on the separating agent layer as band-like rows that intersect a direction of development of the chromatographic medium.

<7> The chromatographic medium according to <6>, wherein bands that form the band-like rows are selected from among straight lines, wavy lines and dashed lines thereof.

<8> The chromatographic medium according to any one of <1> to <7>, wherein the permeation layer is thinner than the separating agent layer.

<9> The chromatographic medium according to any one of <1> to <8>, wherein a separating agent that constitutes the separating agent layer is a separating agent for optical isomers.

<10> The chromatographic medium according to <9>, wherein the separating agent for optical isomers contains a polysaccharide derivative formed of a polysaccharide and one type of group selected from aromatic ester groups, aromatic carbamoyl groups, aromatic ether groups or carbonyl groups that replace some or all of the hydroxyl groups or amino groups in the polysaccharide.

<11> The chromatographic medium according to any one of <1> to <10>, wherein the permeation layer contains a porous material and a fluorescent indicator or coloring reagent as constituent materials.

<12> The chromatographic medium according to <9>, wherein the porous material is silica gel or surface-treated silica gel.

<13> The chromatographic medium according to <11> or <12>, wherein the permeation layer further contains a binder as a constituent material, <14> The chromatographic medium according to any one of <1> to <13>, wherein scale marks and/or characters are present on the permeation layer.

<15> The chromatographic medium according to <14>, wherein the scale marks and/or characters exhibit an optical responsiveness that are different from those of the permeation layer.

<16> The chromatographic medium according to any one of <1> to <15>, having a base material which faces the separating agent layer or the permeation layer and which supports the chromatographic medium.

<17> The chromatographic medium according to any one of <1> to <16>, wherein the chromatographic medium is plate-shaped, cylindrical or columnar.

<18> A TLC plate having the chromatographic medium according to any one of <1> to <15>, and a base material used to support the chromatographic medium, wherein the chromatographic medium is laminated on a plurality of regions on the base material.

<19> A TLC material formed of the chromatographic medium according to any one of <1> to <15>, and a base material used to support the chromatographic medium.

In the chromatographic medium of the present invention, the permeation layer, which is used to enable the permeation of the separated target substances, is laminated so as to face the separating agent layer, and because this permeation layer exhibits an optical responsiveness that is different from those of the separating agent layer, target substances present in a separating agent layer, which cannot be detected by means of optical responsiveness and which exhibit the same optical responsiveness as the separating agent layer, permeate into the permeation layer and can therefore be detected by means of the optical responsiveness of the target substances that permeate into the permeation layer.

In addition, in the chromatographic medium of the present invention, because a region in which the permeation layer is not laminated is present on a part of the separating agent layer, the target substances appear as spots in this region, and when developing is carried out, it is possible to minimize tailing of the target substances, which can occur as a result of interactions between the separating agent layer and the permeation layer or as a result of the retention of the target substances by the permeation layer.

In addition, because the chromatographic medium of the present invention can achieve the separation and detection of target substances using a single kit, without the need for other components, a complicated procedure is not required to separate and detect the target substances.

BRIEF DESCRIPTION OF THE DRAWINGS

FIG. 1 (a) is a drawing (photograph) showing the spots obtained by using the TLC plate produced in Example 1 (the region from the developing solution dip end part to 1/6.6th of the length of the TLC plate in the direction of development was not laminated with the permeation layer) and developing trans-stilbene oxide (t-SO), Tröger's base and a flavanone using hexane/ethanol (90:10, v/v) as a developing solution, and FIG. 1 (b) is a photograph obtained by carrying out the same procedure as that carried out in Example 1, except that the TLC plate produced in Comparative Example 1 was used.

FIG. 2 (a) is a drawing (photograph) showing the spots obtained by using the same TLC plate as that produced in Example 1 and developing the same target substances as those in Example 1 using ethanol as a developing solution (Example 2), and FIG. 2 (b) is a photograph obtained by carrying out the same procedure as that carried out in Example 1, except that the TLC plate produced in Comparative Example 2 was used.

FIG. 3 (a) is a drawing (photograph) showing the spots obtained by using the TLC plate obtained in Example 3 (a) (silica gel was used as the material that constitutes the permeation layer, and the region from the developing solution dip end part to 1/6.6th of the length of the TLC plate in the direction of development was not laminated with the permeation layer) and developing benzoin ethyl ether (BEE), trans-stilbene oxide (t-SO), Tröger's base and a flavanone using hexane/ethanol (90:10, v/v) as a developing solution, and FIG. 3 (b) is a drawing (photograph) showing the spots obtained by using the TLC plate obtained in Example 3 (b) (aminopropylsilylated silica gel was used as the material that constitutes the permeation layer, and the region from the developing solution dip end part to 1/6.6th of the length of the TLC plate in the direction of development was not laminated with the permeation layer) and developing the same target substances as in Example 3 (a) using the same developing solution as that used in Example 3 (a).

FIG. 4 (a) is a drawing (photograph) showing the spots obtained by using the TLC plate obtained in Example 4 (a) (silica gel was used as the material that constitutes the permeation layer, and the region from the developing solution dip end part to 1/6.6th of the length of the TLC plate in the direction of development was not laminated with the permeation layer) and developing the same target substances as in Example 3 using hexane/isopropyl alcohol (2-propanol) (90:10, v/v) as a developing solution, and FIG. 4 (b) is a drawing (photograph) showing the spots obtained by using the TLC plate obtained in Example 4 (b) (aminopropylsilylated silica gel was used as the material that constitutes the permeation layer, and the region from the developing solution dip end part to 1/6.6th of the length of the TLC plate in the direction of development was not laminated with the permeation layer) and developing the same target substances as in Example 4 (a) using the same developing solution as that used in Example 4 (a).

FIG. 5 (1) is a schematic view of the chromatographic medium of the present invention, which has a region in which the permeation layer is not laminated on a part of the separating agent layer and in which the permeation layer is laminated in the dotted manner on the separating agent layer, and FIG. 5 (2) is a schematic view of the chromatographic medium of the present invention, in which a region in which the permeation layer is not laminated has an approximately circular shape.

FIGS. 6 (1) to 6 (4) are drawings showing examples in which the permeation layer is laminated as band-like rows.

FIG. 7 is a drawing showing an example of the diameter (φ) and pitch (Pt) of dots in a case where the permeation layer is laminated in the dotted manner in the chromatographic medium of the present invention.

FIG. 8 (a) is a schematic view showing a cross-section of one embodiment of the plate-like shape of the chromatographic medium of the present invention, and FIG. 8 (b) is a schematic view showing a cross section of another embodiment of the plate-like shape of the chromatographic medium of the present invention.

FIG. 9 is a schematic view showing one embodiment of a cylindrical shape (FIG. 9 (b)) and columnar shape (FIGS. 9 (a) and 9 (c)) of the chromatographic medium of the present invention.

FIG. 10 is a schematic view showing a TLC plate in which the chromatographic medium of the present invention is laminated in a plurality of regions on a single base material.

FIG. 11 is a schematic view showing a TLC material that contains the chromatographic medium of the present invention and a base material as constituent elements.

MODES FOR CARRYING OUT THE INVENTION

The chromatographic medium of the present invention has a separating agent layer and a permeation layer that is used to enable permeation of target substances separated by the separating agent.

The chromatographic medium of the present invention is obtained by laminating the above-mentioned separating agent layer and permeation layer and encompasses plate-shaped, cylindrical and columnar chromatographic media, with a plate-shaped chromatographic medium being a so-called thin layer chromatography (TLC) medium. Meanwhile, cylindrical or columnar chromatographic media are also known as stick columns.

The aforementioned permeation layer is laminated so as to face the aforementioned separating agent layer, and in a chromatographic medium having the aforementioned permeation layer and separating agent layer, a region is present in which the aforementioned permeation layer is not laminated on a part of the aforementioned separating agent layer. In addition, the aforementioned separating agent layer exhibits a separating property for target substances and also exhibits an optical responsiveness to ultraviolet rays. Meanwhile, the aforementioned permeation layer exhibits an optical responsiveness to ultraviolet rays that is different from those of the target substances and the separating agent layer.

Examples of target substances used in the present invention include optical isomers. Exhibiting a separating property for the target substances means having the capacity to separate the target substances and, in cases where the target substances are optical isomers, means exhibiting optical resolution properties. In addition, in the present invention, an optical responsiveness to ultraviolet rays means a luminescence caused by ultraviolet rays, such as fluorescence, or absorption of ultraviolet rays.

By having the separating agent layer and permeation layer as described above, the chromatographic medium of the present invention enables the target substances that have been separated by the separating agent layer to permeate into the permeation layer. In addition, because the optical responsiveness of the permeation layer differ from the optical responsiveness of the target substances and the separating agent layer, it is possible to verify the target substances that have permeated into the permeation layer by irradiating with ultraviolet rays or the like.

In the chromatographic medium of the present invention, a region is present in which the permeation layer is not present in a part of the separating agent layer. In cases where the target substances are developed by spotting in such a region, it is possible to minimize the broadening of target substance peaks, which can occur as a result of interactions between the separating agent layer and the permeation layer or as a result of retention of the target substances by the permeation layer.

Moreover, the aforementioned part of the separating agent layer in which the permeation layer is not present is not particularly limited in terms of size, shape and position in the chromatographic medium as long as a region remains in which the separation of the target substances by the separating agent layer and confirmation of the target substances in the permeation layer can be achieved to the utmost extent and spotting of the target substances is possible in this region.

From the perspective of ensuring satisfactory separation of the target substances, it is preferable for the region in which the aforementioned permeation layer is not laminated on the aforementioned separating agent layer to be present in the region of the aforementioned chromatographic medium between a dip end part (hereinafter also referred to as the bottom edge), which is dipped in the developing solution used to develop the aforementioned target substances, and half the length of the chromatographic medium in the direction of development.

From the perspective of ensuring good separation of the target substances, it is more preferable for the region in which the aforementioned permeation layer is not laminated to be the region between the bottom edge of the aforementioned chromatographic medium and 1/20 to 1/2.2 of the length of the chromatographic medium in the direction of development. The boundary of this type of region should be provided further to the downstream side, in the direction of development, than the spotting positions of the target substances and the dipping position when the chromatographic medium is dipped in the developing bath.

In addition, from the perspective of productivity, it is preferable for the shape and position of the region in which the aforementioned permeation layer is not laminated on a part of the aforementioned separating agent layer to be a square shape that includes the bottom edge in cases where the chromatographic medium is plate-shaped.

Alternatively, this region may be an approximately circular shape having a size that allows spotting of the target substances to occur.

In addition, the region in which the permeation layer is not laminated does not need to be the whole of the region having the specific range mentioned above, and the permeation layer may be partially laminated in the region having a specific range mentioned above as long as this does not adversely affect the separation characteristics of target substances.

The ratio of the area of the region in which the permeation layer is not laminated relative to the total area of the separating agent layer is preferably 0.05% to 50%, and more preferably 0.2% to 40%, from the perspective of being able to confirm the separation of a wide variety of target substances.

This type of region in which the permeation layer is not laminated and the separating agent layer is exposed can be obtained by laminating the separating agent layer and then, when laminating the permeation layer by using the coating techniques, dipping techniques or printing techniques described later, not coating, dipping or printing only this region.

Alternatively, this type of region can be obtained by laminating the permeation layer on the whole of the separating agent layer and then removing the permeation layer from the separating agent layer by means of a procedure such as scraping.

If the chromatographic medium of the present invention has a constitution such as that described above, the shape thereof is not particularly limited, and can be plate-shaped, cylindrical or columnar.

An example of a plate-shaped chromatographic medium is one having a first embodiment, in which a material such as that described later is used as a base material and the permeation layer, the separating agent layer and the base material are laminated in that order when viewed from the direction in which ultraviolet rays is irradiated (see FIG. 8 (*a*)), or a second embodiment, in which a material such as that described later is used as a base material and the base material, the permeation layer and the separating agent layer are laminated in that order when viewed from the direction in which ultraviolet rays is irradiated (see FIG. 8(*b*)).

In the aforementioned first embodiment, spotting of the target substances occurs in the region where the separating agent layer is exposed on the surface that is irradiated with ultraviolet rays.

A flexible material such as that shown in FIG. 8 (*b*) is used as the base material in the aforementioned second embodiment, and forming the base material so as to be in contact with the separating agent layer and the permeation layer, as shown in FIG. 8 (*b*), is preferred from the perspective of preventing the separating agent layer and permeation layer from disintegrating.

In addition, in the aforementioned second embodiment, spotting of target substances can occur from the direction opposite to the direction in which the ultraviolet rays are irradiated, as shown in FIG. 8 (*b*) (5' in FIG. 8 (*b*)), but it is also possible to remove a part of the base material and carry out spotting from the same direction as the direction in which the ultraviolet rays are irradiated (5 in FIG. 8 (*b*)).

In cases where the chromatographic medium of the present invention is a plate-shaped TLC medium, the aforementioned base material can be a known base material used in TLC. Examples of such basic materials include glass, resin, metal and paper plates. The shape of the base material is not particularly limited, but rectangular plates commonly used in TLC are preferred.

Meanwhile, examples of cylindrical and columnar chromatographic media include those shown in FIG. 9. In these examples, the shape of the cross-section in a direction perpendicular to the axis is elliptical or circular, but this shape is not limited to these, and may be polygonal. These embodiments include embodiments in which the separating agent layer and the permeation layer are formed on the outer peripheral surface of a columnar or cylindrical base material and embodiments in which the separating agent layer and the permeation layer are formed on the inner peripheral surface of a cylindrical base material. A columnar base material can be, for example, a rod having a polygonal or circular cross-sectional shape, and a cylindrical base material can be, for example, a tube having a polygonal cross-sectional shape, a column tube or a tube having the same dimensions as a column tube.

In cases where the separating agent layer and the permeation layer are laminated on the inner peripheral surface of a cylindrical base material, it is possible to verify target substances by using a light-transmissive base material as the cylindrical base material. Here, light-transmissive means a degree of transparency by which it is possible to verify the optical characteristics (coloration, luminescence, light absorption and so on) of spots of the target substances. Examples of tubes such as column tubes having such light transmission properties include quartz glass tubes and tubes made from fluororesins such as PFA {tetrafluoroethylene-perfluoroalkyl vinyl ether copolymers).

In addition, it is possible to obtain a liquid-permeable chromatographic medium which is formed only of a separating agent layer and a permeation layer and which does not have a base material.

In the cylindrical or columnar chromatographic media shown in FIG. 9 also, the target substances are spotted in the region in which the permeation layer is not laminated and the separating agent layer is exposed.

This type of cylindrical or columnar chromatographic medium generally has a length of 1 to 40 cm and a diameter (maximum diameter) of 0.1 to 1 cm.

The separating agent used in the separating agent layer in the chromatographic medium of the present invention is not particularly limited as long as the agent exhibits a separating property for the target substances and exhibits an optical responsiveness to ultraviolet rays.

The above-mentioned separating agent can be a particulate separating agent. Examples of such particulate separating agents include particles formed only of the separating agent and particles obtained by supporting the separating agent on a particulate carrier. The separating agent can be supported on the carrier by physical adsorption or by chemical bonding to the carrier.

The separating agent can be a low molecular weight separating agent or polymer-type separating agent that exhibits an optical responsiveness. Examples of low molecular weight separating agents include ligand exchange type separating agents, charge transfer (n-n) type separating agents, hydrogen bonding type separating agents, clathrate type separating agents, ionic bonding type separating agents, intercalation type separating agents, crown ethers and derivatives thereof, and cyclodextrin and derivatives thereof. Examples of polymer type separating agents include polysaccharide derivatives, polyamides, polymethacrylate esters, polyacrylamides, proteins and tartaric acid derivatives.

Examples of the aforementioned polysaccharide derivative include polysaccharide derivatives formed of a polysaccharide and one type of group selected from aromatic ester groups, aromatic carbamoyl groups, aromatic ether groups or carbonyl groups that replace some or all of the hydroxyl groups or amino groups in the polysaccharide, which are used in separating agents for optical isomers, and examples of these include phenylcarbamate derivatives of cellulose, phenyl ester derivatives of cellulose, phenylcarbamate derivatives of amylose and phenyl ester derivatives of amylose. The phenyl groups in these derivatives may have one or more substituent groups selected from the group consisting of hydrocarbons having 1 to 20 carbon atoms and halogen atoms.

From the perspective of increasing the separation performance, the aforementioned carrier is preferably a porous material. Examples of the aforementioned carrier include synthetic polymers such as crosslinked polystyrene, crosslinked acrylic polymers and epoxy polymers, polysaccharides such as cellulose, crosslinked cellulose strengthened by crosslinking cellulose, crosslinked agarose, crosslinked dextran and crosslinked mannan, and inorganic materials such as alumina, silica gel, mesoporous silica gel, zeolites, diatomaceous earth, fused silica, clay minerals, zirconia and metals.

The particle diameter of the separating agent can be decided according to the objects being separated by the chromatographic medium, and is preferably 10 pin or higher, more preferably 10 to 100 μm, and further preferably 20 to 100 μm. The particle diameter of the separating agent can be the average particle diameter as measured using an ordinary particle diameter measurement device, but catalog values may also be used. Meanwhile, in cases where the separating agent is used to, for example, monitor a synthesis reaction, it is possible to use a separating agent having a particle diameter of lower than 10 μm if a higher degree of separated spot separation is required. In this type of intended use, the particle diameter of the separating agent is preferably 2 to 8 μm, and more preferably 3 to 6 μm.

In cases where the chromatographic medium is a plate-shaped TLC medium, the separating agent layer can be formed by using a known method used to produce a TLC plate, for example by coating a slurry that contains the aforementioned separating agent and a coating solvent on the surface of a support body by using a spreader or by spraying the aforementioned slurry onto the surface of the support body, thereby immersing (dipping) the support body in the aforementioned slurry that contains the separating agent and coating solvent.

In cases where the chromatographic medium is cylindrical, it is possible to obtain a chromatographic medium in which the permeation layer is laminated on the separating agent layer and a tube such as a column tube is present on the peripheral wall of the permeation layer by, for example, forming the material that constitutes the permeation layer on the inner surface of the column tube by coating or printing and then filling with a material that contains the separating agent and a binder or the like so as to form the separating agent layer.

Meanwhile, in cases where the chromatographic medium is columnar, it is possible to obtain a chromatographic medium in which the separating agent layer is laminated on the base material and the permeation layer is laminated on the separating agent layer by, for example, coating a material that contains the separating agent and a binder on the peripheral surface of a rod-like base material or coating a slurry that contains the separating agent and a coating solvent on a rod-like base material, thereby forming the separating agent layer, and then laminating the material that constitutes the permeation layer on the peripheral surface of the separating agent layer by coating or printing.

In addition, an example of a case in which the chromatographic medium is formed as a column without using a pre-formed base material is an embodiment such as that described below.

First, a columnar porous material having the aforementioned separating agent on at least the surface thereof is formed. This type of porous material can be formed from a columnar porous material formed of the separating agent or from a columnar porous material formed of a carrier and the aforementioned separating agent supported on the porous material.

The columnar porous material formed of the separating agent can be formed by using, for example, the method disclosed in Japanese Patent Application Publication No. H4-93336 A, in which a porous material is formed by mixing a separating agent with plastic particles that are soluble in a solvent in which particles of the separating agent are insoluble, molding the obtained mixture by thermal press molding, and then removing insoluble plastic from the obtained molded body by means of solvent treatment.

The aforementioned columnar porous material formed of a carrier can be formed by binding carrier particles or by porosifying a columnar body formed of a carrier, and a porous material obtained by binding carrier particles can be formed using the aforementioned method in cases where the carrier particles are an organic compound such as a polymer or polysaccharide. The aforementioned porous material obtained by porosifying a columnar porous material formed of a carrier can be formed by using, for example, the method of Japanese Patent No. 3397255 B or 3317749 B or a so-called sol-gel method.

The separating agent can be supported on the aforementioned columnar porous material formed of a carrier by, for example, using a known method for modifying the surface of pores in the porous material by physically adsorbing or chemically bonding the separating agent to the carrier.

It is possible to obtain a liquid-permeable columnar chromatographic medium by forming the permeation layer by laminating the material that constitutes the permeation layer by means of coating or printing on the peripheral surface of the columnar porous material, which has the aforementioned separating agent on at least the surface thereof and which is produced by using the procedure described above.

The aforementioned coating solvent can be water, an organic solvent or a mixed solvent thereof. The organic solvent can be an alcoholic solvent, a glycol ether-based solvent, a hydrocarbon-based solvent, a ketone or an ester. For example, it is possible to use α-terpineol, butyl carbitol acetate, butyl carbitol, toluene, cyclohexane, methyl ethyl ketone or methylpropylene glycol.

As the aforementioned coating solvent, a mixed solvent of water and a water-soluble organic solvent is preferred and a mixed solvent of water and an alcohol is more preferred. The content of alcohol in the aforementioned mixed solvent is preferably 0.1 to 50 mass %, more preferably 1 to 45 mass %, and further preferably 2 to 40 mass %.

Examples of alcohols able to be used include ethanol, 1-propanol, 2-propanol, 1-butanol, 2-butanol, 2-methyl-1-propanol, 2-methyl-2-propanol, 1-pentanol and 3-methyl-3-methoxybutanol.

The content of the coating solvent in the aforementioned slurry can be decided in view of the uniformity of the formed separating agent layer, the thickness of this layer and economic factors, and is preferably 10 to 5000 parts by mass, more preferably 50 to 1000 parts by mass, and further preferably 100 to 300 parts by mass, relative to 100 parts by mass of the separating agent.

If this content falls within such a range, it is possible to use not only a slurry-like material that exhibits a high fluidity, but also a material having a low coating solvent content and a high viscosity when producing, for example, a cylindrical or columnar chromatographic medium.

From the perspective of improving the strength of the formed separating agent layer, it is preferable for the aforementioned slurry to further contain a binder. The aforementioned binder can be a component that imparts binding properties that enable a layer of the separating agent to be formed on the surface of the base material. Examples of such binders include inorganic binders such as gypsum and colloidal silica, organic fibers such as microfibrillated cellulose, thickening agents such as alkaline water-soluble copolymers, hydroxyethyl cellulose and carboxymethyl cellulose, and organic binders such as poly(vinyl alcohol) and acrylic acid. It is possible to use a single binder or a combination of two or more types thereof.

The content of the binder in the aforementioned slurry can be decided as appropriate according to the type of binder and by taking into account the strength of the formed separating agent layer and the ability to obtain a suitable ascension rate of the mobile phase in the separating agent layer. In the case of gypsum, for example, the content of the binder is preferably 0.1 to 50 parts by mass, more preferably 1 to 30 parts by mass, and further preferably 1 to 20 parts by mass, relative to 100 parts by mass of the separating agent. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the separating agent.

From the perspective of achieving satisfactory separation characteristics, the thickness of the separating agent layer in the chromatographic medium of the present invention is preferably 20 to 5000 μm, and more preferably 50 to 3000 μm.

In addition, from the perspective of maintaining good sample separation performance, it is preferable for the thickness of the permeation layer to be less than the thickness of the separating agent layer in the chromatographic medium of the present invention.

From the perspective of maintaining good sample separation performance, it is preferable for the ratio of the thickness of the separating agent layer to the thickness of the permeation layer in the present invention to be such that if the thickness of the separating agent layer is 1, the thickness of the permeation layer is preferably 0.002 to 0.8, more preferably 0.005 to 0.5 and particularly preferably 0.006 to 0.4.

The aforementioned permeation layer exhibits an optical responsiveness that is different from those of the target substances and the separating agent layer. Here, "different optical responsiveness" means that one optical response caused by irradiation by ultraviolet rays or coloration by a coloring reagent and another optical response differ in terms of the degree to which optical recognition is possible as a result of color or brightness.

In addition, the permeation layer is a layer into which at least a part of the component that forms a spot in the separating agent layer permeates.

In addition, it is important that the material that constitutes the permeation layer has no effect on the separation characteristics of the target substances in the separating agent layer on the chromatographic medium, that is, has no effect on the distribution of the target substances between the mobile phase and the separating agent layer, in order to prevent spots of the target substances on the chromatographic medium from becoming broad.

As a result, in cases where, for example, the separating agent used in the separating agent layer is supported on a carrier, it is preferable for the material that constitutes the permeation layer to be the same as the material of the carrier. In addition, the material that constitutes the permeation layer can be one selected as appropriate from among those materials described later that do not affect the distribution of the target substances between the mobile phase and the separating agent layer.

The aforementioned permeation layer is laminated on the aforementioned separating agent layer, but it is preferable for the permeation layer to be laminated in a discontinuous manner in the direction of development of the chromatographic medium in order to reduce the bypass effect that is an interaction between the separating agent layer and the permeation layer, prevent spots of the target substances from becoming broad and achieve good separation (hereinafter also referred to as separation characteristics). In the present invention, laminated in a discontinuous manner means that the aforementioned permeation layer is laminated with intervals, not laminated continuously, in the direction of development of the chromatographic medium, and these intervals may or may not be the same size.

In order to enable permeation of the target substances and obtain sufficient resolution to detect the target substances, these intervals are preferably 0.015=t or larger, more preferably 0.02 mm or larger, and particularly preferably 0.05 mm or larger. However, in order to suppress interactions with the separating agent layer caused by diffusion of the target substances into the permeation layer and ensure good separation of the target substances, these intervals 'are preferably 4 mm or smaller, more preferably 3 mm or smaller, and particularly preferably 2 mm or smaller.

In addition, in order to enable permeation of the target substances and ensure sufficient area for detecting the target substances, the ratio of the volume of voids in the permeation layer (the sum of the volume of voids inside the material (internal voids) and the volume of voids among the material (external voids)) relative to the volume of the overall layer is preferably 0.1 to 0.9, and more preferably 0.2 to 0.8.

In addition, it is preferable for the permeation layer in the chromatographic medium of the present invention to be laminated in the dotted manner on the aforementioned separating agent layer. In the present invention, a dotted manner is a pattern formed from a multiplicity of discontinuous points or sub-regions in shapes that may be, for example, circular, roughly circular, roughly elliptical, or a roughly polygonal shape, such as a roughly triangular or roughly quadrangular shape in which each side can be straight or curved, and the size and density of the dots is not particularly limited. From the perspective of standardizing the separation characteristics of the target substances in the chromatographic medium, it is preferable for the shape of the dots to be regular. Furthermore, it is preferable for the arrangement of dots to be regular.

From the perspective of permeability of the target substances, it is particularly preferable for the dots to be circular or approximately circular in shape, and from the perspective of standardizing the separation characteristics of target substances in the chromatographic medium, as mentioned above, it is preferable for the arrangement of the dots to be regular, as shown in FIGS. 5 and 6.

In cases where the dots are circular in shape, the average diameter of the dots is preferably 0.01 to 5 mum, more preferably 0.01 to 4 mm, further preferably 0.02 to 3 mm, and particularly preferably 0.05 to 1 mm, from the perspectives of permeability of target substances and separation characteristics.

Meanwhile, in cases where the dots are not circular in shape, the average diameter of the maximum diameter is preferably 0.02 to 6 mm, more preferably 0.05 to 5 mm, and further preferably 0.05 to 1.5 mm, for the same reasons as those given for cases where the dots are circular in shape.

In the present invention, maximum diameter means the length of the longest axis in the case of, for example, elliptical dots, but more commonly means the maximum value of the distance between two parallel planes in cases where the shape is viewed from above and held by the two planes in an arbitrary direction.

In addition, in cases where the permeation layer is laminated in the dotted manner, the interval (pitch) between dots is preferably 0.01 to 6 mm, more preferably 0.01 to 4 mm, further preferably 0.02 to 3 mm, and particularly preferably 0.05 to 1 mm, from the perspectives of reducing interactions with the separating agent layer and improving the resolution when the detecting target substances permeate into the permeation layer.

In cases where the dots are circular in shape, the pitch between dots is preferably 0.01 to 6 mm, more preferably 0.02 to 3 mm, further preferably 0.05 to 1 mm, and particularly preferably 0.06 to 1 mm, for the same reasons as those given above.

In addition, when expressed in terms of lines per inch {number of dots per inch}, the dot density is preferably 5 to 2000, more preferably 10 to 400, and further preferably 20 to 300.

In addition to the dot-like pattern mentioned above, a preferred embodiment of the permeation layer in the chromatographic medium of the present invention is one in which the permeation layer is laminated as band-like rows that intersect the direction of development of the chromatographic medium. By laminating in this way, it is possible to ensure the satisfactory separation characteristics of the target substances and achieve the satisfactory permeation of the target substances into the permeation layer.

The shape of the bands that form the aforementioned band-like rows can be straight lines, wavy lines or dashed lines thereof. The width of these bands is not particularly limited, but is preferably 0.01 to 15 mm, and more preferably 0.02 to 10 mum, from the perspectives of ensuring the separation characteristics of the target substances and obtaining sufficient resolution to detect the target substances.

In addition, the interval between bands is not particularly limited, but it is preferable for the intervals between bands to be equal from the perspective of obtaining uniform separation characteristics of the target substances, and this interval is preferably 0.01 to 3 mm, and more preferably 0.02 to 2 mm.

The material that constitutes the permeation layer in the chromatographic medium of the present invention can be a porous material.

From the perspective of ensuring the satisfactory permeation of the target substances, this type of porous material is one in which the pore volume, as measured by a gas adsorption method, is preferably 0.1 ml/g or higher, more preferably 0.2 ml/g or higher, and particularly preferably 0.3 to 0.9 ml/g.

Porous materials having a pore volume such as that mentioned above can be a commercially available silica gel or ceramic in which the catalog value for the pore volume satisfies the range mentioned above, which are the preferred porous materials mentioned below, and it is possible to adjust the pore volume of a porous material that contains silica by treating the material with an aqueous solution of hydrogen fluoride or an aqueous solution of an alkali, and it is possible to adjust the pore volume of a ceramic by adjusting the firing conditions during granulation or treating with an acidic solution.

In addition, from the perspective of preventing the aggregation of a slurry that contains the porous material, the particle diameter of the porous material is preferably 0.1 μm or higher, more preferably 1 μm or higher, and particularly preferably 2 μm or higher. Meanwhile, from the perspectives of permeability when screen printing a slurry containing this porous material and the finish of the surface of the permeation layer, the upper limit for the particle diameter of the porous material is preferably 100 μm or lower, more preferably 70 μm or lower, and particularly preferably 50 μm or lower.

The particle diameter of the porous material can be the average particle diameter as measured using an ordinary particle diameter measurement device, but catalog values may also be used.

Examples of porous materials able to be used in the present invention include silica gel, mesoporous silica gel, zeolites, cellulose, diatomaceous earth, fused silica, clay minerals, alumina, zirconia, other ceramics, for example ceramics obtained by subjecting a variety of clay minerals, such as sepiolite, attapulgite, palygorskite, talc, which contains $SiO_2$ and MgO as primary components, kaolinite, which contains $SiO_2$ as a primary component, and montmorillonite, to crushing, granulating, acid treatment (if necessary) and firing. It is possible to use commercially available products of these porous materials, and it is also possible to use porous materials in which the catalog values for the pore volume and particle diameter are as described above.

Of these, it is preferable to use porous materials having the above-mentioned pore volume and particle diameter, and it is preferable to use silica gel from the perspective of affinity with solvents.

The types of silica gel that can be used in the present invention include silica gel that has been surface-treated with a silane coupling agent, for example silica gel that has been modified by octadecylsilyl groups or aminopropylsilyl groups. This type of surface-treated silica gel tends not to affect the distribution of the target substances between the separating agent layer and the mobile phase, and is therefore preferably used.

In addition, selecting a material that does not affect the distribution of the target substances between the separating agent layer and the mobile phase as the above-mentioned porous material is preferred from the perspective of preventing spots of the target substances on the chromatographic medium from becoming broad.

In addition, the material that constitutes the permeation layer in the chromatographic medium of the present invention may be the fluorescent indicators or coloring reagents mentioned later. In addition, it is also possible to obtain the permeation layer by laminating a composition obtained by mixing these fluorescent indicators or coloring reagents with a binder and, if necessary, a support body having a particle diameter of 0.1 to 100 μm, such as a glass, plastic, metal or ceramic.

The content of the binder in such a composition can be decided as appropriate according to the type of binder used and by taking into account the strength of the formed permeation layer and the ability to reduce the bypass effect that is an interaction between the separating agent layer and the permeation layer in the permeation layer. In the case of gypsum, for example, the content of the binder is preferably 0.1 to 50 parts by mass, more preferably 0.5 to 30 parts by mass, and further preferably 1 to 20 parts by mass, relative to 100 parts by mass of the fluorescent indicator or coloring reagent. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the fluorescent indicator or coloring reagent.

In addition, in cases where the aforementioned support body is incorporated, the content thereof is preferably 0.1 to 0.9 parts by mass, more preferably 0.2 to 0.8 parts by mass, and particularly preferably 0.3 to 0.7 parts by mass, relative to 100 parts by mass of the fluorescent indicator or coloring reagent.

The permeation layer in the chromatographic medium of the present invention can be laminated using a variety of methods. For example, in cases where the chromatographic medium is a plate-shaped TLC medium and the permeation layer contains a porous material as a constituent material, the permeation layer can be produced by coating a slurry that contains the porous material on the separating agent layer of the TLC plate and then drying the slurry. In addition, the same method can also be used in cases where the permeation layer is obtained from the fluorescent indicators or coloring reagents described below or from a composition that contains these fluorescent indicators or coloring reagents, a binder and, if necessary, a support body.

In the chromatographic medium of the present invention, if the permeation layer is laminated in a discontinuous manner in the direction of development of the chromatographic medium, the permeation layer can be laminated by using, for example, a printing process.

Examples of printing processes include screen printing, such as silk screen printing, and ink jet printing.

In the case of screen printing, it is possible to use, as a screen printing plate, a plate having the shape described in the above-mentioned lamination mode as the shape of the openings (a plate having discontinuous openings in the direction of development of the chromatographic medium or a plate having variously shaped dots or band-like rows as openings). It preferable to use a screen printing process, such as silk screen printing, due to the ability to laminate the permeation layer inexpensively using a simple procedure.

The material for the screen printing plate is not limited as long as a slurry that contains the porous materials described later can be used as a printing ink. An example of this type of screen printing plate is a metal mask.

Meanwhile, in cases where ink jet printing is used, it is possible to use a slurry that contains the porous materials described later as the ink used for the printing, but it is also possible to use a commonly used ink jet printing process.

Meanwhile, in cases where a cylindrical or columnar chromatographic medium is produced, the chromatographic medium can be produced by coating a slurry that contains a porous material on the separating agent layer and then drying the slurry. In addition, in cases where the permeation layer is obtained from a fluorescent indicator or coloring reagent or from a composition that contains a fluorescent indicator or coloring reagent, a binder and, if necessary, a support body, the same method can be used.

In the cylindrical or columnar chromatographic medium, if the permeation layer is laminated in a discontinuous manner in the direction of development of the chromatographic medium, the permeation layer can be laminated by using, for example, a printing process. This type of printing process can be the screen printing described above, and the screen printing plate is preferably a flexible plate having the openings described above and is preferably wound on the peripheral surface of the separating agent layer.

In cases where this type of screen printing process is used, by providing a desired opening part, such as a character or scale mark, on the screen printing plate, the permeation layer is not laminated on that part of the permeation layer, meaning that the separating agent layer is exposed, and because the separating agent layer exhibits an optical responsiveness that is different from those of the permeation layer, it is possible to verify the character or scale mark when irradiating with ultraviolet rays. In this way, it is possible to increase the usefulness of the chromatographic medium.

In order to ensure a satisfactory permeation and prevent the permeation layer from being affected by the optical responsiveness of the separating agent layer when detecting spots of the target substances when using a transparent or semitransparent porous material, the thickness (average thickness) of the permeation layer obtained by coating the slurry or by the above-mentioned printing process is preferably 0.005 mm or higher, and more preferably 0.01 mm or higher.

Meanwhile, from the perspective of preventing the diffusion of the spots of the target substances, the thickness (average thickness) of the permeation layer is preferably 0.2 mm or lower, and more preferably 0.15 mm or lower.

In order to laminate the permeation layer on the separating agent layer, it is possible to use the coating or printing processes described above, but in these processes, it is possible to prepare a slurry that contains a porous material, a solution that contains a fluorescent indicator or coloring reagent or a composition that contains a fluorescent indicator or coloring reagent, a binder and, if necessary, a support body, and then use this slurry, solution or composition as a coating liquid or ink.

The materials used when preparing a slurry that contains a porous material include solvents and, if necessary, binders. Such solvents and binders can be the same as those used when preparing the separating agent layer.

Examples of the above-mentioned fluorescent indicator include magnesium tungstate and manganese-containing zinc silicate, and examples of solvents able to be used when preparing a solution or slurry that contains the above-mentioned fluorescent indicators include organic solvents, such as alcoholic solvents, glycol ether-based solvents, hydrocarbon-based solvents, ketones or esters, that are used as screen printing ink solvents. For example, it is possible to use α-terpineol, butyl carbitol acetate, butyl carbitol, toluene, cyclohexane, methyl ethyl ketone or methylpropylene glycol. In order to prevent the fluidity of the slurry from deteriorating during printing and prevent screen clogging, an appropriate solvent is selected in view of its physical properties such as fluidity, boiling point and evaporation rate.

Meanwhile, examples of coloring reagents include anisic aldehyde solutions, phosphomolybdic acid solutions, iodine solutions, ninhydrin solutions, chameleon solutions, DNPH solutions, manganese chloride solutions and bromocresol green solutions.

When using a composition that contains a fluorescent indicator or coloring reagent, a binder and, if necessary, a support body, it is possible to obtain a coating liquid or printing ink by dissolving or suspending the above-mentioned binder in a solution of the above-mentioned fluorescent indicator or coloring reagent.

When incorporating a porous material as a constituent material that forms the permeation layer, it is possible to use an organic solvent, such as an alcoholic solvent, a glycol ether-based solvent, a hydrocarbon-based solvent, a ketone or an ester, as the solvent used in the slurry that contains the porous material. For example, in cases where an alcohol is used, a mixed solvent of water and a water-soluble organic solvent is preferred and a mixed solvent of water and an alcohol is more preferred. The content of alcohol in the aforementioned mixed solvent is preferably 0.1 to 50 mass %, more preferably 1 to 45 mass %, and further preferably 2 to 40 mass %.

Examples of alcohols able to be used include ethanol, 1-propanol, 2-propanol, 1-butanol, 2-butanol, 2-methyl-1-propanol, 2-methyl-2-butanol, 1-pentanol and 3-methyl-3-methoxybutanol.

The content of the solvent in the aforementioned slurry can be decided in view of the uniformity of the formed permeation layer, the thickness of this layer and economic factors, and is preferably 10 to 5000 parts by mass, more preferably 50 to 1000 parts by mass, and further preferably 100 to 300 parts by mass, relative to 100 parts by mass of the porous material.

From the perspective of improving the strength of the formed permeation layer, it is preferable for the aforementioned slurry to further contain a binder. The aforementioned binder may be a component that imparts binding properties that enable a layer of the porous material to be formed on the surface of the separating agent layer. Examples of such binders include inorganic binders such as gypsum and colloidal silica, organic fibers such as microfibrillated cellulose, thickening agents such as alkaline water-soluble copolymers, hydroxyethyl cellulose and carboxymethyl cellulose, and organic binders such as poly(vinyl alcohol) and acrylic acid. It is possible to use a single binder or a combination of two or more types thereof.

The content of the binder in the aforementioned slurry can be decided as appropriate according to the type of binder used and by taking into account the strength of the formed permeation layer and being able to obtain a suitable ascension rate of the mobile phase from the separating agent layer to the permeation layer. In the case of gypsum, for example, the content of the binder is preferably 0.1 to 50 parts by mass, more preferably 0.5 to 30 parts by mass, and further preferably 1 to 20 parts by mass, relative to 100 parts by mass of the porous material. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the porous material.

In cases where a porous material is contained as a constituent material of the permeation layer, when detecting spots by means of the optical responsiveness brought about by irradiation with ultraviolet rays, it is possible to impart the permeation layer with an optical responsiveness by incorporating a fluorescent indicator in the slurry that contains the porous material. This type of fluorescent indicator can be a known fluorescent indicator, for example the aforementioned magnesium tungstate and manganese-containing zinc silicate. The content of the fluorescent indicator can be set within a range whereby separation of the target substances is possible, and is preferably 0.1 to 10 parts by mass, and particularly preferably 1 to 8 parts by mass from the perspective of optimizing the contrast between the target substances and the permeation layer, relative to 100 parts by mass of the aforementioned porous material.

In addition, in cases where a porous material is contained as a constituent material of the permeation layer, when detecting the spots by means of a color-producing reaction, it is possible to impart the permeation layer with an optical responsiveness by incorporating a coloring reagent in the slurry that contains the porous material. This type of coloring reagent can be known, such as phosphomolybdic acid, ninhydrin, or the like. The content of the coloring reagent can be set within a range whereby separation of the target substances is possible, and is preferably 0.1 to 10 parts by mass, and particularly preferably 1 to 8 parts by mass from the perspective of optimizing the contrast between the target substances and the permeation layer, relative to 100 parts by mass of the aforementioned porous material.

In addition, the present invention also provides a TLC plate in which the above-mentioned chromatographic medium is laminated in a plurality of regions on a single base material (see FIG. 10). According to this type of TLC plate, it is possible to laminate various combinations of separating agent layers and permeation layers on a single base material, and also possible to observe the target substance separation characteristics using a single developing solution. With regard to the method of laminating the separating agent layer or permeation layer, in the case of a plurality of the target chromatographic media, it is possible for layers to be overlaid in such a way as to be in contact with each other, but it is also possible to use the method described above.

In addition, the present invention also provides a TLC material in which a separating agent layer and a permeation layer are laminated on a single base material and which has a region in which the permeation layer is not laminated on the edges of the base material, as shown schematically in FIG. 11 (see FIG. 11). According to this type of TLC material, it is possible to obtain the TLC plate shown in FIG. 5, which has a base material, a separating agent layer and a permeation layer and which has a region in which the permeation layer is not laminated on a part of the separating agent layer, by, for example, providing grooves at the positions shown by the dashed lines in FIG. 11 and cutting this TLC material along these grooves by using an appropriate method, such as snapping by hand or cutting with a plate cutter.

For the base material, separating agent layer and permeation layer used here and the methods for laminating these layers, it is possible to use the features described above. In addition, the positions where the grooves are provided in the TLC material are not particularly limited.

The chromatographic medium of the present invention can achieve the separation and detection of target substances in a sample by using a method that is essentially the same as the methods that use conventional TLC plates, even though the shape of the medium varies from aspect to aspect. However, the spotting of a sample should be made in a region where the permeation layer is not laminated.

Separation and detection of the target substances in a sample can be achieved by using a method that includes a step of developing the sample by using a mobile phase in the direction of development of the chromatographic medium (in cases where the chromatographic medium is a TLC plate, this direction is preferably the longitudinal direction when using a rectangular medium), a step of drying the mobile phase on the chromatographic medium, and a step of detecting the spots of the migrated components of the target substances by irradiating with ultraviolet rays or by a coloration treatment using a coloring reagent.

By developing a sample with a mobile phase by using the chromatographic medium of the present invention, the target substances in the sample are separated as the target substances permeate into the permeation layer on the separating agent layer.

Moreover, the target substances in the present invention exhibit an optical responsiveness that is different from those of the permeation layer and exhibit an optical responsiveness that is the same as those of the separating agent layer.

By using the chromatographic medium of the present invention, it is possible to achieve the separation and optical detection of the extract component and the raffinate component of the target substances in the sample using a single chromatography process. Comparing with a conventional TLC plate having two separating agent layers, the conventional plate had the problem of the target substance peaks becoming broad due to the differences in the migration rates of the components of the target substances in the sample between the separating agent layers, whereas with the present invention, this type of problem does not occur and the raffinate component and extract component can both be reliably detected. In addition, if the chromatographic medium of the present invention has a plate-like shape, it is possible to reliably detect the state of separation of each sample when the spots of a plurality of samples are applied in a line and developed simultaneously. In addition, it is possible to select a region (including the separating agent layer) that includes a specific spot that has permeated into the permeation layer and use this region to isolate components of the target substances by carrying out an extraction process.

EXAMPLES

Example 1

Firstly, a first slurry was prepared by adding 4.00 g of a Chiralpak IA (registered trademark) manufactured by Daicel Corporation ("IA Filler"), 0.60 g of gypsum, 4.00 g of an aqueous solution containing 2% of 1110 grade CMC (carboxymethyl cellulose, manufactured by Daicel Corporation) and 0.60 g of an aqueous solution containing 20% of Snowtex C (manufactured by Nissan Chemical Industries, Ltd.) to a mixed solution containing 0.40 g of water and 1.60 g of ethanol, and then stirring vigorously while irradiating with ultrasonic waves.

In addition, a second slurry was prepared by adding 2.00 g of silica gel (IR-60-5/20-U, liquid chromatography grade manufactured by Daiso), 2.00 g of an aqueous solution containing 3% of 1110 grade CMC (carboxymethyl cellulose, manufactured by Daicel Corporation) and 0.08 g of a manganese-containing zinc silicate to a mixed solution containing 1.42 g of water and 1.20 g of ethanol, and then stirring vigorously while irradiating with ultrasonic waves.

Of these slurries, a separating agent layer formed of the first slurry was laminated by uniformly coating the first slurry on the surface of 6 glass plates arranged in series by means of a TLC plate preparation spreader, drying the first slurry layer, and then vacuum drying at 60° C. for 3 hours by using a vacuum pump. Next, the second slurry was coated on the separating agent layer by using a metal mask (manufactured by Tokyo Process Service Co. Ltd.). A plate having regular circular openings with diameters of 0.4 mm at a pitch of 0.6 mm (see FIG. 5) was used as a screen printing plate. Moreover, a TLC plate 1, in which a permeation layer that was a layer of the second slurry was laminated in the dotted manner on the separating agent layer, was prepared by uniformly coating the second slurry from the bottom edge of the TLC plate, excluding a region having a length of 1.5 cm from the bottom edge in the direction of development of the TLC plate, drying the second slurry layer and then vacuum drying at 60° C. for 3 hours by using a vacuum pump.

The TLC plate 1 had a width of 5 cm and a length of 10 cm. In this way, the permeation layer was not present and the separating agent layer was exposed in a region between the bottom edge of the TLC plate and 1/6.6th of the length of the TLC plate in the direction of development (up to 1.5 cm from the bottom edge of the TLC plate). In the TLC plate 1, the thickness of the separating agent layer was 150 μm and the thickness of the permeation layer was 20 μm.

The separating agent layer formed of the first slurry was a layer formed of the IA filler, and the permeation layer formed of the second slurry was a layer of the aforementioned silica gel. In addition, the average particle diameter of the IA filler was 20 μm and the average particle diameter of the silica gel was 14.4 μm.

Approximately 3 μL of an ethyl acetate solution containing 1% of a racemate of trans-stilbene oxide (t-SO), 1% of a racemate of Tröger's base (TB) and 1% of a racemate of a flavanone (FLV) was applied as a spot to a position approximately 3.0 cm from the bottom, if the direction of development of the TLC plate 1 is taken to be vertical (a region in which the permeation layer was not present). The TLC plate 1 was placed, with the sample spot downwards, in a developing bath containing a mixed solvent of n-hexane and ethanol at a volume ratio of 9:1 as a developing solution, and optical isomers of the trans-stilbene oxide, Tröger's base and flavanone in the sample were developed in the direction of development of the TLC plate 1.

Following this developing, the TLC plate 1 was dried with cold air, and when the TLC plate 1 was irradiated with ultraviolet rays, spots of the raffinate component (Rt-SO) and extract component (Et-SO) of trans-stilbene oxide, spots of the raffinate component (RTB) and extract component (ETB) of Tröger's base, and spots of the raffinate component (RFLV) and extract component (EFLV) of the flavanone were confirmed as dark brown-black spots on the permeation layer (see FIG. 1).

The Rf value for each spot was determined from the position at which the sample was applied on the permeation layer, the position reached by the developing solution and the position of the center of the spot. Furthermore, the k' value was determined from the relationship k'=(1−Rf)/Rf. Furthermore, the a value was determined by using the k' value. The results for these optical isomers are shown in Table 1.

Comparative Example 1

A TLC plate 3 was prepared using the same raw materials and procedure as those used in Example 1, except that the region in which the permeation layer was not present on the TLC plate of Example 1 was not provided and the permeation layer was provided over the entire surface of the separating agent layer. In addition, optical isomers of the trans-stilbene oxide, Tröger's base and flavanone were developed using the same procedure and developing solution as those used in Example 1, except that the spotting of the target substances was carried out on the permeation layer. Next, the Rf value for each spot was determined in the same way as in Example 1 from the position at which the sample was applied on the permeation layer, the position reached by the developing solution and the position of the center of the spot. Furthermore, the k' value was determined from the relationship k'=(1−Rf)/Rf. Furthermore, the a value was determined by using the k' value. The results for these optical isomers are shown in Table 1.

TABLE 1

| | Example 1 | | | Comparative Example 1 | | |
| --- | --- | --- | --- | --- | --- | --- |
| | t-SO | TB | FLV | t-SO | TB | FLV |
| Rf1 | 0.66 | 0.49 | 0.41 | 0.66 | 0.48 | 0.44 |
| Rf2 | 0.58 | 0.41 | 0.33 | 0.58 | 0.41 | 0.34 |
| α | 1.41 | 1.38 | 1.41 | 1.41 | 1.33 | 1.53 |
| k'1 | 0.52 | 1.04 | 1.44 | 0.52 | 1.08 | 1.27 |
| k'2 | 0.72 | 1.44 | 2.03 | 0.72 | 1.44 | 1.94 |

Example 2

Optical isomers of the trans-stilbene oxide, Tröger's base and flavanone in the sample were developed in the direction of development of the TLC plate 1 using the same procedure as that used in Example 1, except that a TLC plate 2, which was prepared using the same raw materials and procedure as those used for TLC plate 1 prepared in Example 1, was used and methanol was used as the developing solution. Next, the Rf value, k' value and a value for each spot was determined in the same way as in Example 1 from the position at which the sample was applied on the permeation layer, the position reached by the developing solution and the position of the center of the spot. The results for these optical isomers are shown in Table 2.

Comparative Example 2

A TLC plate 4 was prepared using the same raw materials and procedure as those used in Example 1, except that the region in which the permeation layer was not present on the TLC plate of Example 1 was not provided and the permeation layer was provided over the entire surface of the separating agent layer. In addition, optical isomers of the trans-stilbene oxide, Tröger's base and flavanone were developed using the same procedure as that used in Example 1, except that the spotting of the target substances was carried out on the permeation layer and methanol was used as the developing solution. Next, the Rf value for each spot was determined in the same way as in Example 1 from the position at which the sample was applied on the permeation layer, the position reached by the developing solution and the position of the center of the spot. Furthermore, the k' value was determined from the relationship $k'=(1-Rf)/Rf$. Furthermore, the a value was determined by using the k' value. The results for these optical isomers are shown in Table 2.

TABLE 2

|  | Example 2 | | | Comparative Example 2 | | |
| --- | --- | --- | --- | --- | --- | --- |
|  | t-SO | TB | FLV | t-SO | TB | FLV |
| Rf1 | 0.58 | 0.53 | 0.51 | 0.55 | 0.50 | 0.46 |
| Rf2 | 0.53 | 0.39 | 0.38 | 0.48 | 0.39 | 0.35 |
| α | 1.22 | 1.76 | 1.70 | 1.32 | 1.56 | 1.58 |
| k'1 | 0.72 | 0.89 | 0.96 | 0.82 | 1.00 | 1.17 |
| k'2 | 0.89 | 1.56 | 1.63 | 1.08 | 1.56 | 1.86 |

From the results obtained in Examples 1 and 2 and Comparative Examples 1 and 2, it was understood that good target substance separation characteristics are obtained in cases where the permeation layer is not provided and the separating agent layer is exposed in a specific length range from the bottom edge of the TLC plate and the target substances are developed after being applied to this exposed separating agent layer.

Example 3 (a)

Benzoin ethyl ether, trans-stilbene oxide, Tröger's base and flavanone were developed using the same procedure and developing solution (a mixed solvent of n-hexane and ethanol at a volume ratio of 9:1) as those used in Example 1, by using a TLC plate 5, which was prepared using the same raw materials and procedure as those used for TLC plate 1 prepared in Example 1. Next, the Rf value for each spot was determined in the same way as in Example 1 from the position at which the sample was applied on the permeation layer, the position reached by the developing solution and the position of the center of the spot. Furthermore, the k' value was determined from the relationship $k'=(1-Rf)/Rf$. Furthermore, the a value was determined by using the k' value. The results for these optical isomers are shown in Table 3.

Example 3 (b)

Benzoin ethyl ether, trans-stilbene oxide, Tröger's base and flavanone were developed using the same procedure and developing solution (a mixed solvent of n-hexane and ethanol at a volume ratio of 9:1) as those used in Example 1, by using a TLC plate 6, which was prepared using the same raw materials and procedure as those used for TLC plate 1 prepared in Example 1, except that the silica gel incorporated in the second slurry, which was a raw material used to produce TLC plate 1 prepared in Example 1, was an aminopropylsilylated silica gel (IR-60-5/20-APS, manufactured by Daiso). Next, the Rf value, k' value and a value for each spot was determined in the same way as in Example 1 from the position at which the sample was applied on the permeation layer, the position reached by the developing solution and the position of the center of the spot. The results for these optical isomers are shown in Table 3.

TABLE 3

|  | Example 3(a) | | | | Example 3(b) | | | |
| --- | --- | --- | --- | --- | --- | --- | --- | --- |
|  | t-SO | TB | FLV | BEE | t-SO | TB | FLV | BEE |
| Rf1 | 0.68 | 0.48 | 0.38 | 0.56 | 0.65 | 0.51 | 0.40 | 0.59 |
| Rf2 | 0.60 | 0.40 | 0.29 | 0.49 | 0.55 | 0.43 | 0.30 | 0.51 |
| α | 1.42 | 1.38 | 1.50 | 1.32 | 1.52 | 1.38 | 1.56 | 1.38 |
| k'1 | 0.47 | 1.08 | 1.63 | 0.79 | 0.54 | 0.96 | 1.50 | 0.69 |
| k'2 | 0.67 | 1.50 | 2.45 | 1.04 | 0.82 | 1.33 | 2.33 | 0.96 |

Example 4 (a)

Benzoin ethyl ether, trans-stilbene oxide, Tröger's base and flavanone were developed using the same procedure as that used in Example 1, except that a TLC plate 7, which was prepared using the same raw materials and procedure as those used for TLC plate 1 prepared in Example 1, was used and a mixed solvent containing n-hexane and isopropyl alcohol (2-propanol) at a volume ratio of 9:1 was used as the developing solution. Next, the Rf value, k' value and a value for each spot was determined in the same way as in Example 1 from the position at which the sample was applied on the permeation layer, the position reached by the developing solution and the position of the center of the spot. The results for these optical isomers are shown in Table 4.

Example 4 (b)

Benzoin ethyl ether, trans-stilbene oxide, Tröger's base and flavanone were developed using the same procedure as that used in Example 1, except that a TLC plate 8, which was prepared using the same raw materials and procedure as those used for TLC plate 1 prepared in Example 1, except that the silica gel incorporated in the first slurry, which was a raw material used to produce TLC plate 1 prepared in Example 1, was an aminopropylsilylated silica gel (IR-60-5/20-APS, manufactured by Daiso), was used and a mixed solvent containing n-hexane and isopropyl alcohol (2-propanol) at a volume ratio of 9:1 was used as the developing solution. Next, the Rf value, k' value and α value for each spot was determined in the same way as in Example 1 from the position at which the sample was applied on the permeation layer, the position reached by the developing solution and the position of the center of the spot. The results for these optical isomers are shown in Table 4.

TABLE 4

|     | Example 4(a) | | | | Example 4(b) | | | |
| --- | --- | --- | --- | --- | --- | --- | --- | --- |
|     | t-SO | TB | FLV | BEE | t-SO | TB | FLV | BEE |
| Rf1 | 0.69 | 0.48 | 0.44 | 0.60 | 0.68 | 0.54 | 0.43 | 0.56 |
| Rf2 | 0.49 | 0.43 | 0.39 | 0.54 | 0.45 | 0.45 | — | 0.51 |
| α | 2.32 | 1.22 | 1.23 | 1.28 | 2.60 | 1.43 | — | 1.22 |
| k'1 | 0.45 | 1.08 | 1.27 | 0.67 | 0.47 | 0.85 | 1.33 | 0.79 |
| k'2 | 1.04 | 1.33 | 1.56 | 0.85 | 1.22 | 1.22 | — | 0.96 |

From the results obtained using Examples 3 and 4, it was understood that the cases in which a surface-treated silica gel was used instead of silica gel as a material that constitutes the permeation layer were equivalent or superior in terms of the target substance separation characteristics to cases in which silica gel was used.

INDUSTRIAL APPLICABILITY

TLC has been used in the past as an important means for investigating the separation conditions in column chromatography and has also been used to isolate target substances. Because the present invention enables the state of separation of the target substances to be detected more reliably and simply than in the past by using a separating agent, by which the detection of the state of separation by the optical response characteristics was difficult, it is expected that the present invention will contribute to a further expansion of applications for this type of separating agent and to a further development of separation and purification techniques that use this type of separating agent.

EXPLANATION OF REFERENCE SYMBOLS t-SO: trans-stilbene oxide
TB: Tröger's base
FLV: Flavanone
BEE: Benzoin ethyl ether
1: Permeation layer
2: Separating agent layer
3: Base material
4: Direction of irradiation with ultraviolet rays
5, 5': Spotting direction

The invention claimed is:

1. A chromatographic medium comprising:
a base layer;
a first layer comprising a permeation layer for enabling the permeation of at least one target substance to be separated by a separating agent layer and disposed in a first plane, the permeation layer containing a porous material and a fluorescent indicator or coloring reagent as constituent materials; and
a second layer comprising a separating agent layer for separating the at least one target substance and disposed in a second plane different from the first plane, wherein the separating agent layer is laminated to the base layer,
the at least one target substance, the separating agent layer and the permeation layer all exhibit an optical responsiveness to ultraviolet rays, the permeation layer exhibits an optical responsiveness to ultraviolet rays different from the at least one target substance and the separating agent layer and the permeation layer is laminated to a region of a surface of the separating agent layer by applying a slurry containing the porous material and the fluorescent indicator or coloring reagent and then drying the slurry and not laminated to another region of the surface of the separating agent layer.

2. The chromatographic medium according to claim 1, wherein a region in which the permeation layer is not laminated to the separating agent layer is present in the middle or half-way point of the chromatographic medium in a direction of development.

3. The chromatographic medium according to claim 1, wherein the permeation layer is thinner in depth than the separating agent layer.

4. The chromatographic medium according to claim 1, wherein a separating agent that constitutes the separating agent layer is a separating agent for optical isomers.

5. The chromatographic medium according to claim 4, wherein the separating agent for optical isomers contains a polysaccharide derivative formed of a polysaccharide and one type of group selected from the group consisting of aromatic ester groups, aromatic carbamoyl groups, aromatic ether groups and carbonyl groups that replace some or all of hydroxyl groups or amino groups in the polysaccharide.

6. The chromatographic medium according to claim 4, wherein the porous material is silica gel or surface-treated silica gel.

7. The chromatographic medium according to claim 1, wherein the permeation layer further contains a binder as a constituent material.

8. The chromatographic medium according to claim 1, comprising a base material which faces the separating agent layer or the permeation layer.

9. The chromatographic medium according to claim 1, wherein the chromatographic medium is plate-shaped, cylindrical or columnar.

10. A TLC material comprising:
the chromatographic medium according to claim 1; and
a base material for supporting the chromatographic medium.

* * * * *